(12) United States Patent
Onoe et al.

(10) Patent No.: US 8,417,304 B2
(45) Date of Patent: Apr. 9, 2013

(54) BIOLOGICAL INFORMATION MEASURING APPARATUS

(75) Inventors: Atsushi Onoe, Tsurugashima (JP); Yoshinori Kimura, Tsurugashima (JP)

(73) Assignee: Pioneer Corporation, Tokyo (JP)

( * ) Notice: Subject to any disclaimer, the term of this patent is extended or adjusted under 35 U.S.C. 154(b) by 0 days.

(21) Appl. No.: 12/532,108

(22) PCT Filed: Mar. 20, 2007

(86) PCT No.: PCT/JP2007/055611
§ 371 (c)(1),
(2), (4) Date: Sep. 18, 2009

(87) PCT Pub. No.: WO2008/114398
PCT Pub. Date: Sep. 25, 2008

(65) Prior Publication Data
US 2010/0105994 A1    Apr. 29, 2010

(51) Int. Cl.
*A61B 5/1455*    (2006.01)
(52) U.S. Cl. .................. 600/310; 600/344; 600/322
(58) Field of Classification Search ........... 600/309–344
See application file for complete search history.

(56) References Cited

U.S. PATENT DOCUMENTS

| 5,766,131 | A | 6/1998 | Kondo et al. |
| 6,626,835 | B1 * | 9/2003 | Kraus ............................ 600/454 |
| 2004/0193063 | A1 | 9/2004 | Kimura et al. |
| 2008/0097172 | A1 * | 4/2008 | Sawada et al. ................ 600/310 |

FOREIGN PATENT DOCUMENTS

| JP | 62-39703 A | 3/1987 |
| JP | 09-038056 A | 2/1997 |
| JP | 2003-079589 A | 3/2003 |
| JP | 3490433 A | 1/2004 |
| JP | 2004-261366 A | 9/2004 |

* cited by examiner

*Primary Examiner* — Eric Winakur
*Assistant Examiner* — Marjan Fardanesh
(74) *Attorney, Agent, or Firm* — Sughrue Mion, PLLC

(57) ABSTRACT

There is provided a biological information measuring apparatus, which permits to release constriction of capillary vessels a human body to provide stable measurement results of biological information and a proper S/N ratio.
The biological information measuring apparatus 1 includes a beam-emitting type sensor device 10 provided on a mounting unit 2 to optically measure biological information of a subject 4. The beam-emitting type sensor device 10 is placed in a position so as to be in a non-contact state relative to the subject 4 when measuring the biological information.

4 Claims, 9 Drawing Sheets

BIOLOGICAL INFORMATION MEASURING APPARATUS

TECHNICAL FIELD

The present invention relates to a technical field of a biological information measuring apparatus that measures biological information such as a blood velocity, a degree of oxygen saturation and a pulse of a subject.

BACKGROUND OF THE INVENTION

A conventional biological information monitoring system, which is provided with a laser blood flow meter for measuring a blood velocity of a subject, is disclosed in Patent Document 1. More specifically, the biological information monitoring system is provided with the laser blood flow meter, which measures a blood velocity based on a scattering beam caused by a laser beam that is emitted into a body tissue and then scattered within the body tissue.

More specifically, this laser blood flow meter is provided with a receiving case, which receives therein a beam emitting device for emitting a laser beam into a body tissue, a detection device for detecting a scattering beam caused by the laser beam that is emitted by the beam emitting device and then scattered within the body tissue, and a beam condensing device for condensing the above-mentioned scattering beam and enabling the above-mentioned detection device to detect it, wherein a contact surface, which is a part of an outer peripheral surface of the receiving case and comes into contact with a surface of the body tissue when making measurement, is substantially flat.

Patent Document 1: Publication of Japanese Patent No. 3490433

DISCLOSURE OF THE INVENTION

Subject to be Solved by the Invention

Figure 1:
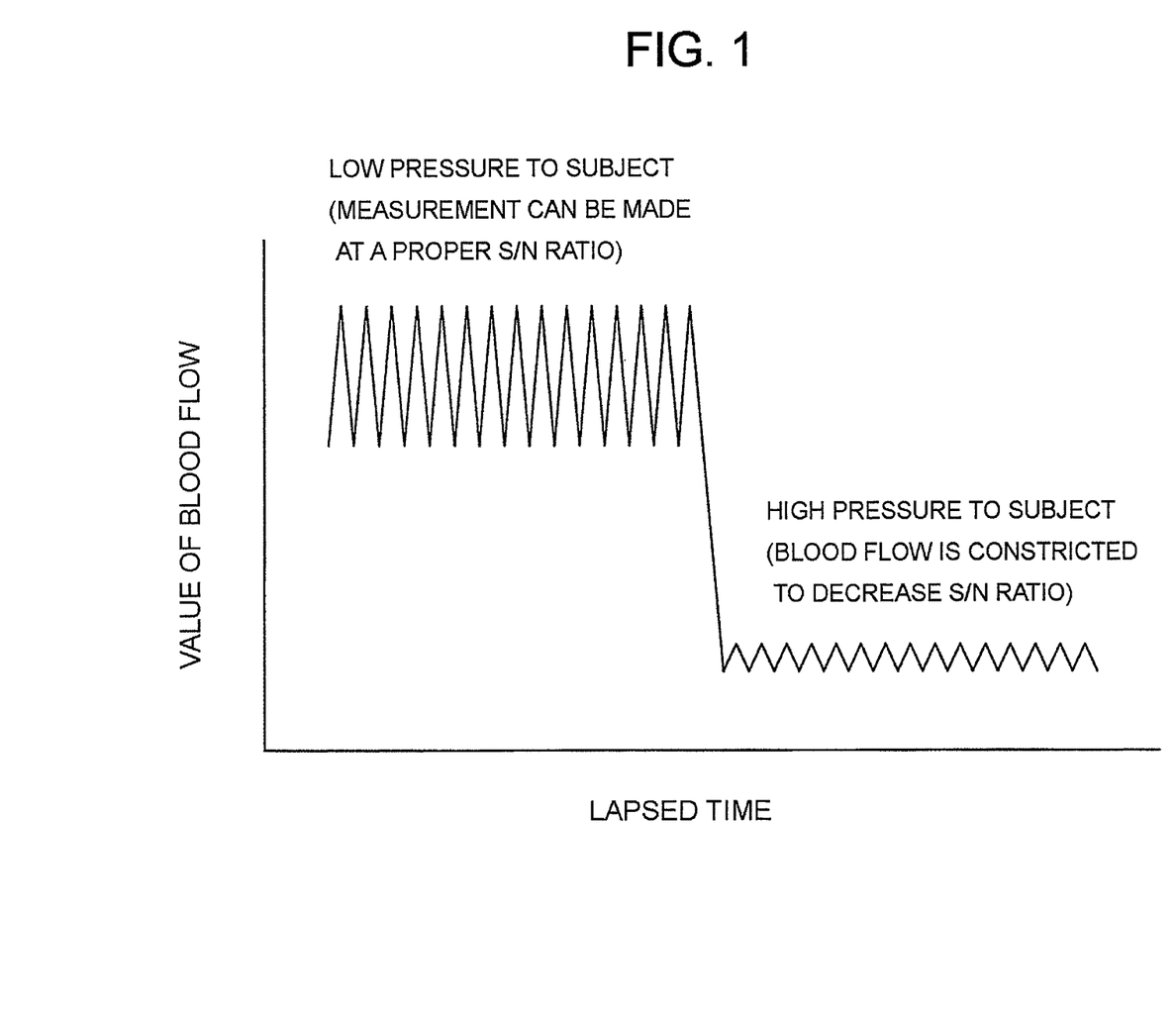
FIG. 1 is a diagram showing a blood flow waveform acquired by a conventional laser blood flow meter.

The laser blood flow meter for the biological information monitoring system disclosed in Patent Document 1 is used to make measurement by placing a skin such as a finger on the contact surface formed on the receiving case so as to be flat and fasten them with a fastening device such as a band. However, when a fastening force by which the skin such as the finger is fasten on the above-mentioned contact surface is excessively large, capillary vessels are forcefully compressed so as to constrict blood flow as shown in FIG. 1, thus leading to decrease in an S/N ratio and difficulty in making an appropriate measurement. Therefore, extreme care should be taken to attach the laser blood flow meter.

Meanwhile, there is a conceivable use to combine such a laser blood flow meter with a device such as a headphone, a headset or the like to reflect a biological information of a human body in an operation of an entertainment device such as a music player. However, the structure of the conventional laser blood flow meter may cause dispersion in attached state thereof due to an attaching method carried out by an individual user, leading to a problem in which an analysis with a proper S/N ratio cannot be made, since the individual user may not always attach the laser blood flow meter in a proper state, unlike a health professional.

Therefore, an object of the present invention, which was made in view of the above-mentioned facts, is, by way of example, to provide a biological information measuring apparatus, which permits to release constriction of capillary vessels to provide stable measurement results and a proper S/N ratio.

Means to Solve the Subject

In order to attain the aforementioned object, a biological information measuring apparatus of claim 1 comprises: a beam-emitting type sensor device provided on amounting unit, the beam-emitting type sensor device being capable of optically measuring biological information of a subject, wherein: the beam-emitting type sensor device is placed in a position so as to be in a non-contact state relative to the subject when measuring the biological information.

In addition, in order to attain the aforementioned object, a biological information measuring apparatus of claim 9 comprises: a beam-emitting type sensor device provided on amounting unit, the beam-emitting type sensor device being capable of optically measuring biological information of a subject, wherein: the beam-emitting type sensor device is provided with an anterior plate having an optical transparency, a part of the anterior plate being in contact with the subject, when measuring the biological information.

EXPLANATION OF THE REFERENCE NUMERALS

1: biological information measuring apparatus
2: receiving member
3: recess
4: subject
5: mounting unit
6: stepped portion
10: beam-emitting type sensor device
11: substrate
12: laser diode
13: photodiode
14: anterior plate
15: signal processing/control circuit

BEST MODE FOR CARRYING OUT THE INVENTION

Now, embodiments of the present invention in the best mode will be described in detail below with reference to the accompanying drawings. The first to seventh embodiments of the present invention will be described as embodiments in which a beam-emitting type sensor device is applied, by way of example, to a field of medical care.

First Embodiment

Figure 2:
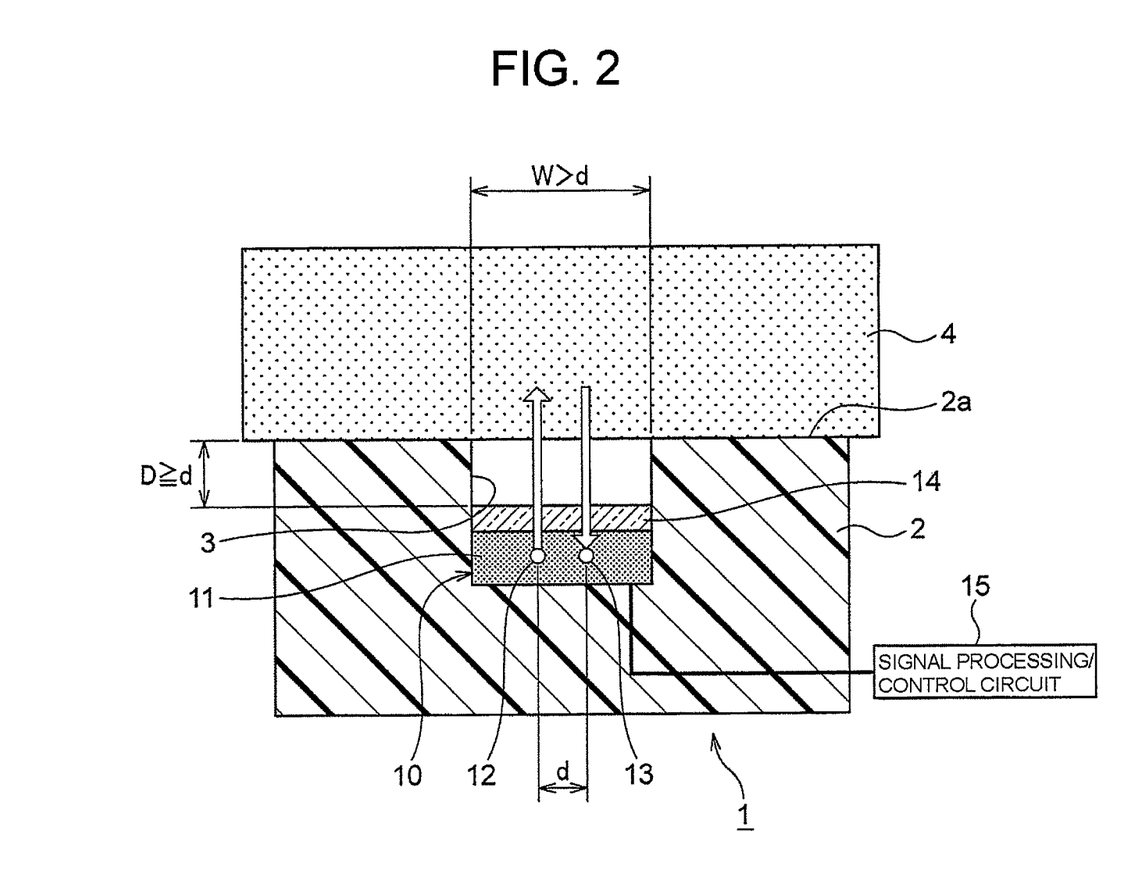
FIG. 2 is a schematic sectional view illustrating a biological information measuring apparatus according to the first embodiment of the present invention.

The biological information measuring apparatus according to the first embodiment of the present invention will be described with reference to FIG. 2. FIG. 2 is a schematic sectional view illustrating the biological information measuring apparatus according to the first embodiment of the present invention.

As shown in FIG. 2, the biological information measuring apparatus 1 comprises a receiving member 2 formed of silicone resin, which serves as an example of a mounting unit. The receiving member 2 has an upper surface, which serves as a contact surface 2a with a human body of a subject 4. The receiving member 2 has a recess 3 formed therein, having a rectangular shape in the plan view. A beam-emitting type sensor device 10, which is capable of optically measuring biological information of the subject 4, is received in the recess 3. A micro sensor is mainly used as the beam-emitting type sensor device 10 in this embodiment.

The beam-emitting type sensor device 10 comprises: a substrate 11 serving as an example of a holding unit; a laser diode 12 serving as an example of a beam emitting section that is placed in the substrate 11 and emits a laser beam to the subject 4; a photodiode 13 serving as an example of a beam receiving section that is placed in the substrate 11 and detects a scattering beam from the subject 4, caused by the laser beam as emitted; and an anterior plate 14 that is placed in front of the laser diode 12 and the photodiode 13 so as to face the subject 4 and has an optical transparency, wherein emitting and receiving of the beam by the respective laser diode 12 and photodiode 13 can be conducted through the anterior plate 14.

Fabry-Perot (FP) type laser or a surface-emitting laser, which is relatively inexpensive, is often used as the semiconductor laser of the laser diode 12. The laser diode 12 and the photodiode 13 are described as being placed in the substrate 11. However, the present invention is not limited only to the substrate 11, and there may be used any thing, which is capable of holding the laser diode 12 and the photodiode 13. In case where the above-mentioned FP type laser is used, the beam is emitted from the end surface. An inclined surface of the laser receiving member (not shown in the figures) may be used as a reflecting surface to emit the beam to the human body. The incoming of the beam emitted from the laser diode 12 directly into the photodiode 13 hinders the intended purpose of detection of the biological information. Accordingly, a not-shown beam shielding wall is preferably placed between the laser diode 12 and the photodiode 13. A reflection film, through which the laser beam cannot be transmitted, or resin is used as material for the beam shielding wall.

The anterior plate 14 has a function of protecting optical devices such as the laser diode 12 and the photodiode 13. In case where the beam emitted from the laser diode 12 is a visible light, a glass plate is used. In case where the beam is an infrared light, a silicone plate is used. The anterior plate 14, which is placed above the photodiode 13, is provided with a not-shown beam shielding film to restrict the beam incoming into the photodiode 13. Thus, only the beam, which travels from the upper side to the lower side in FIG. 2, comes into the photodiode 13. This prevents a beam, which should not be detected, from coming into the photodiode 13, thus improving the detection accuracy. When the above-mentioned beam shielding film is combined for example with a fine pinhole formed in the anterior plate 14 so as to provide a structure having the similar effect, it is possible to prevent surely a beam, which should not be detected, from coming into the photodiode 13.

The beam-emitting type sensor device 10 causes the laser diode 12 to emit a laser beam to a skin of a human body of the subject 4 and the photodiode 13 to receive a scattering beam, which has been scattered by the body tissue such as erythrocytes under the skin and then returned, to measure a blood velocity, a degree of oxygen saturation and the other biological fluid components. The beam-emitting type sensor device 10 is electrically connected to a signal processing/control circuit 15, a not-shown power source, etc. The signal processing/control circuit 15 has a function of amplifying the scattering beam received by the beam-emitting type sensor device 10 and analyzing the amplified scattering beam to determine a blood velocity, etc. The whole or a part of the signal processing/control circuit 15 may be incorporated into the substrate 11. In this case, using silicone as material for the substrate 11 to fabricate an integrated circuit as the substrate would permit to downsize the beam-emitting type sensor device 10.

When a distance between respective centers of the laser diode 12 and the photodiode 13 is determined as "d", a design is made so that the depth "D" of the recess 3 formed in the receiving member 2 is to be equal to or larger than "d", and the recess has the minimum opening width "W", which encompasses at least the laser diode 12 and the photodiode 13. More specifically, on the assumption that the minimum opening width of the recess 3, when viewed from above, is determined as "W", there is a relationship of "W>d".

The distance "d" between the respective centers of the laser diode 12 and the photodiode 13 is set, based on requirements for maintaining the downsizing of the beam-emitting type sensor device 10, as a distance in which the laser beam emitted from the laser diode 12 does not intercept the scattering beam to be received by the photodiode 13.

The receiving member 2 has in the figure an appearance as a member for receiving the beam-emitting type sensor device 10. However, it may be designed as a part of a product into which the beam-emitting type sensor device 10 is to be incorporated to use it. Silicone resin is exemplified as material for the receiving member 2. However, if the beam-emitting type sensor device 10 can be assembled into the product, the receiving member 2 may be formed of the same material such as plastic or metal as the structural component of the product.

Now, operation and effects of the present invention according to the embodiment will be described below.

As shown in FIG. 2, the biological information measuring apparatus 1 according to the embodiment of the present invention is attached to the subject 4 in a state that, for example, the tip of a finger of the subject 4 is placed on the contact surface 2a so as to cross over the opening of the receiving member 2 in which the beam-emitting type sensor device 10 is received.

Then, the laser diode 12 is operated to emit the laser beam from the laser diode 12 and the laser beam passes through the anterior plate 14 to reach the tip of the finger of the subject 4, thereby measuring a blood velocity of the body tissue. In this case, the site emitted with the laser beam is preferably a site in which capillary vessels are densely distributed in a position, which is relatively close to the epidermis (for example, a hand, foot, face or ear).

The laser beam, which has reached the tip of the finger of the subject 4, penetrates into the human body in a predetermined depth and then is scattered by blood of the subject 4 or the body tissue such as cutaneous cells. The scattering beam is collected by a not-shown collecting device such as a lens and then detected by the photodiode 13. Doppler shift takes place in the beam, which is scattered by erythrocytes flowing into blood vessels, resulting in variation in a wavelength of the beam based on a moving velocity of the erythrocytes, i.e., a flow rate of blood. Calculation of a shift amount of Doppler permits to determine the blood velocity.

The photodiode 13 is capable of receiving the scattering beam from the body tissue to determine not only the blood velocity in the above-mentioned body tissue, but also a blood flow rate, an amount of blood, a pulse and the other biological information.

Figure 3:
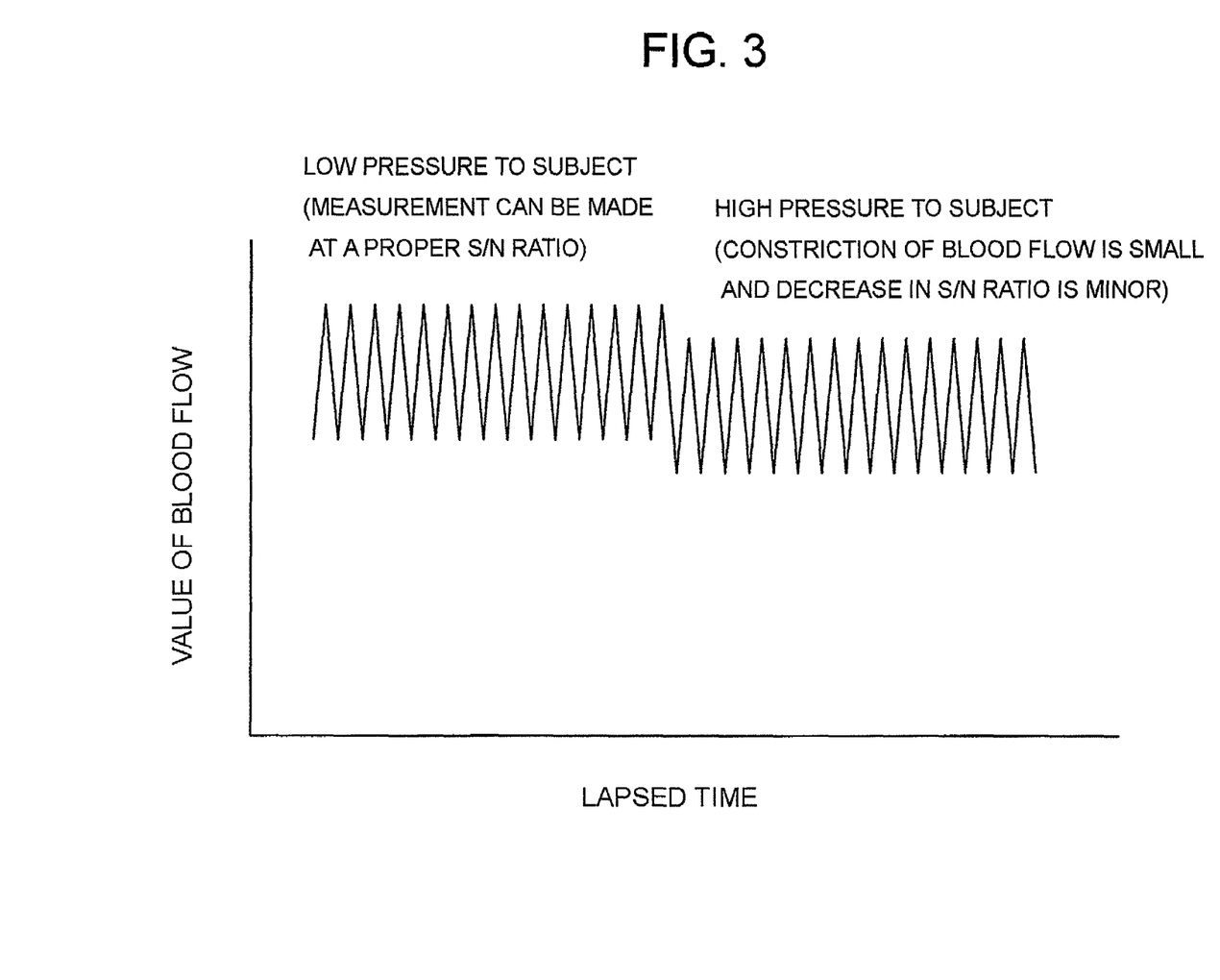
FIG. 3 is a diagram showing a blood flow waveform acquired by the biological information measuring apparatus according to the first embodiment of the present invention.

According to the embodiment of the present invention, the beam-emitting type sensor device 10 is placed in a position so as to be in a non-contact state relative to the subject 4 when measuring the biological information. Therefore, the pressure applied to a portion of the subject 4 to be measured cam be kept low, thus effectively preventing the constriction of the capillary vessels of the human body of the subject 4 to provide stable measurement results of the biological information as shown in FIG. 3 and ensure a proper S/N ratio.

More specifically, in the embodiment of the present invention, the subject 4 comes into contact with the contact surface 2*a* so as to cross over the opening of the recess 3 of the receiving member 2, with the result that the pressure applied to the portion of the subject 4 to be measured cam be kept low. Therefore, it was revealed as shown in FIG. 3 that, in case where the apparatus was attached to the subject 4 with a small pressure applied thereto, the biological information could be measured with a proper S/N ratio, and even in case where the apparatus was attached to the subject 4 with a relatively large pressure applied thereto, there was almost no adverse affect on blood flow in the site as detected, and decrease in S/N ratio was minor.

According to the embodiment of the present invention, the receiving member 2 has the recess 3 having a rectangular shape in the plan view, formed therein, and the beam-emitting type sensor device 10 is received in the above-mentioned recess 3. It is therefore possible to place surely the beam-emitting type sensor device 10 in a position in an easy manner, so as to be in a non-contact state relative to the subject 4.

The embodiment of the present invention utilizes, as the scattering beam, the beam from the subject 4 caused by the emitted beam. The present invention is not limited only to such an embodiment, but may include use of beam as reflected, diffracted, penetrated or Doppler-shifted.

In the embodiment of the present invention, the recess 3 is described as having a rectangular shape in the plan view. The present invention is not limited only to such an embodiment, but the recess may have the other polygonal, circular, elliptic or semi-circular shape in the plan view. This will apply to the embodiments utilizing the recess 3 in the subsequent description of the embodiments.

When, in the embodiment of the present invention, the recess 3 in which the beam-emitting type sensor device 10 is received, is filled with material having a lower hardness than the site to be detected, for example transparent soft material such as flexible rubber, it is possible to prevent the recess from being clogged with foreign substances such as dust. In view of medical purpose, when the recess 3 is filed with transparent liquid, it is possible to provide a stable condition between the beam-emitting type sensor device 10 and the skin of the subject 4, thus permitting a remarkably stable measurement of the human body.

Second Embodiment

Figure 4:
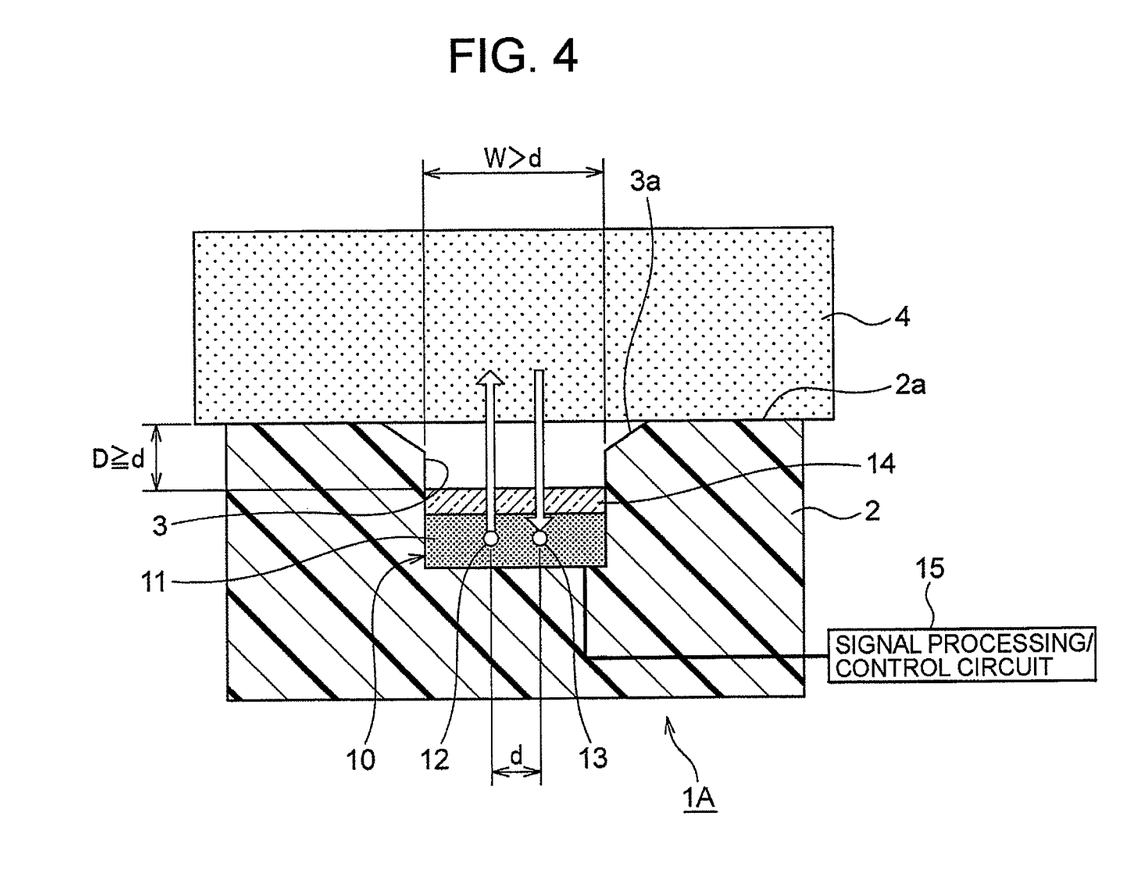
FIG. 4 is a schematic sectional view illustrating the biological information measuring apparatus according to the second embodiment of the present invention.

FIG. 4 is a schematic sectional view illustrating the biological information measuring apparatus according to the second embodiment of the present invention. The description will be given below with the same reference numerals given to the same structural components as those of the first embodiment of the present invention, or the corresponding structural components to those of the first embodiment thereof. This will apply to the other embodiments.

As shown in FIG. 4, the biological information measuring apparatus 1A comprises a receiving member 2 serving as the mounting unit. The receiving member 2 has a recess 3 formed therein, having a rectangular shape in the plan view. A beam-emitting type sensor device 10, which is capable of optically measuring biological information of the subject 4, is received in the recess 3. In this embodiment of the present invention, the recess 3 is provided at an opening peripheral edge thereof with a chamfered portion 3*a*.

In the embodiment of the present invention, formation of the chamfered portion 3*a* at the opening peripheral edge of the recess 3 provides a smaller area of the contact surface 2*a* of the receiving member 2, which comes in contact with the subject 4, than the first embodiment of the present invention as described above, thus leading to a smaller contact area with the subject 4.

The beam-emitting type sensor device 10 comprises: a substrate 11 serving as an example of a holding unit; a laser diode 12 serving as an example of a beam emitting section that is placed in the substrate 11 and emits a laser beam to the subject 4; a photodiode 13 serving as an example of a beam receiving section that is placed in the substrate 11 and detects a scattering beam from the subject 4, caused by the laser beam as emitted; and an anterior plate 14 that is placed in front of the laser diode 12 and the photodiode 13 so as to face the subject 4 and has an optical transparency, wherein emitting and receiving of the beam by the respective laser diode 12 and photodiode 13 can be conducted through the anterior plate 14. The other structure and functions of the beam-emitting type sensor device 10 are the same as those of the first embodiment of the present invention as describe above, and the description of them will be omitted. This will apply to the embodiments utilizing the beam-emitting type sensor device 10 in the subsequent description of the embodiments.

According to the embodiment of the present invention, formation of the chamfered portion 3*a* at the opening peripheral edge of the recess 3 provides a smaller contact area of the receiving member 2 with the subject 4, with the result that the pressure applied to a portion of the subject 4 to be measured cam be kept lower, thus more effectively preventing the constriction of the capillary vessels of the human body of the subject 4 to provide more stable measurement results of the biological information as shown in FIG. 3 and ensure a proper S/N ratio.

When the chamfered portion 3*a* as shown in FIG. 4 has a larger area in the embodiment, it is possible to effectively prevent the recess from being clogged with foreign substances such as dust.

In view of medical purpose, when the recess 3 is filed with transparent liquid in the same manner as the modification of the first embodiment as described above of the present invention, it is possible to provide a stable condition between the beam-emitting type sensor device 10 and the skin of the subject 4, thus permitting a remarkably stable measurement of the human body. This may also apply to the subsequent embodiments in which the recess as formed is utilized.

Third Embodiment

Figure 5:
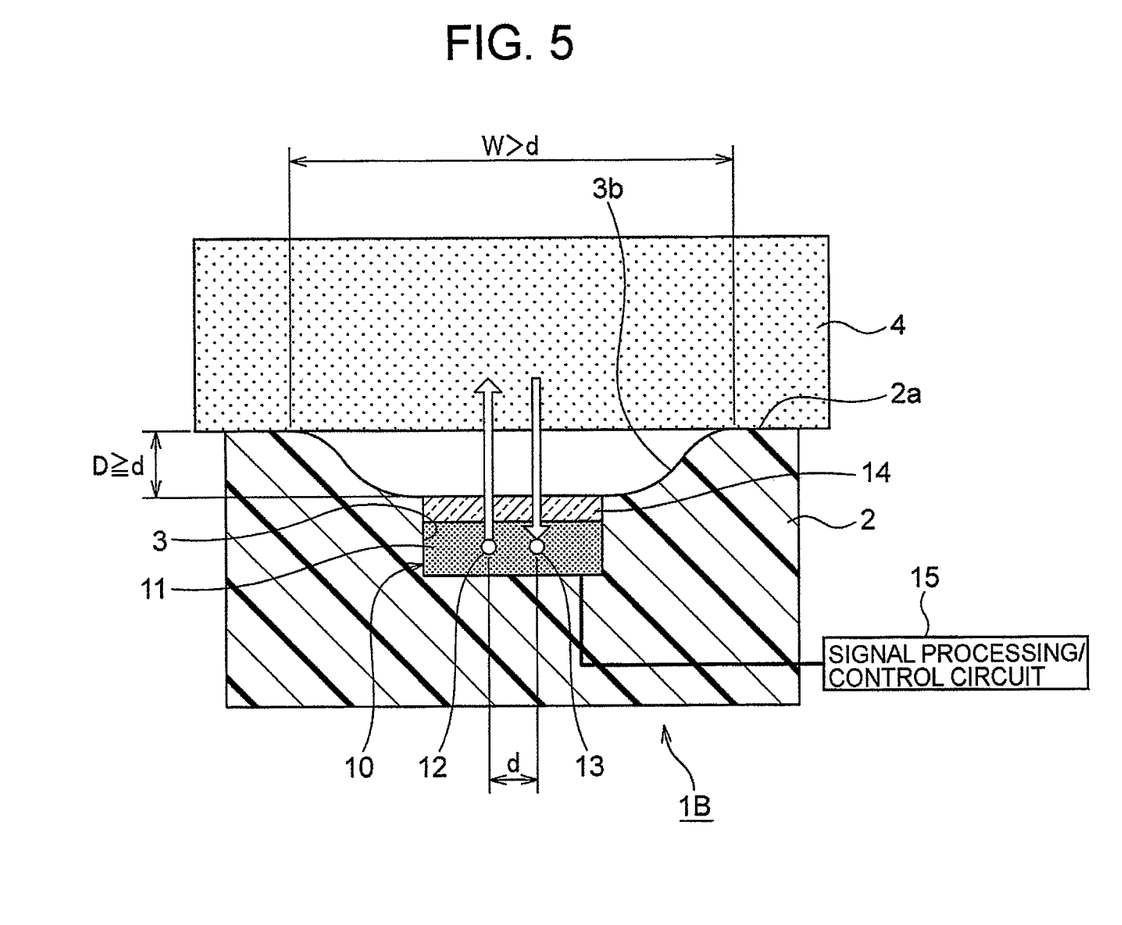
FIG. 5 is a schematic sectional view illustrating the biological information measuring apparatus according to the third embodiment of the present invention.

FIG. 5 is a schematic sectional view illustrating the biological information measuring apparatus according to the third embodiment of the present invention.

As shown in FIG. 5, the biological information measuring apparatus 1B comprises a receiving member 2 serving as the mounting unit. The receiving member 2 has a recess 3 formed therein. A beam-emitting type sensor device 10, which is capable of optically measuring biological information of the subject 4, is received in the recess 3.

In this embodiment of the present invention, the recess 3 is provided at an opening peripheral edge thereof with a gently inclined surface 3b. The inclined surface 3b extends in a gently curved shape from the contact surface of the receiving member 2, which is to come contact with the subject 4, to the anterior plate 14 of the beam-emitting type sensor device 10.

According to the embodiment of the present invention, formation of the gently inclined surface 3b at the opening peripheral edge of the recess 3 provides a smaller contact area of the receiving member 2 with the subject 4, with the result that the pressure applied to a portion of the subject 4 to be measured cam be kept lower in the same manner as the second embodiment of the present invention as described above, thus more effectively preventing the constriction of the capillary vessels of the human body of the subject 4 to provide more stable measurement results of the biological information and ensure a proper S/N ratio.

In this embodiment of the present invention, the recess 3 is provided at the opening peripheral edge thereof with the gently inclined surface 3b. It is therefore possible to effectively prevent the recess 3 from being clogged with foreign substances such as dust.

Fourth Embodiment

Figure 6:
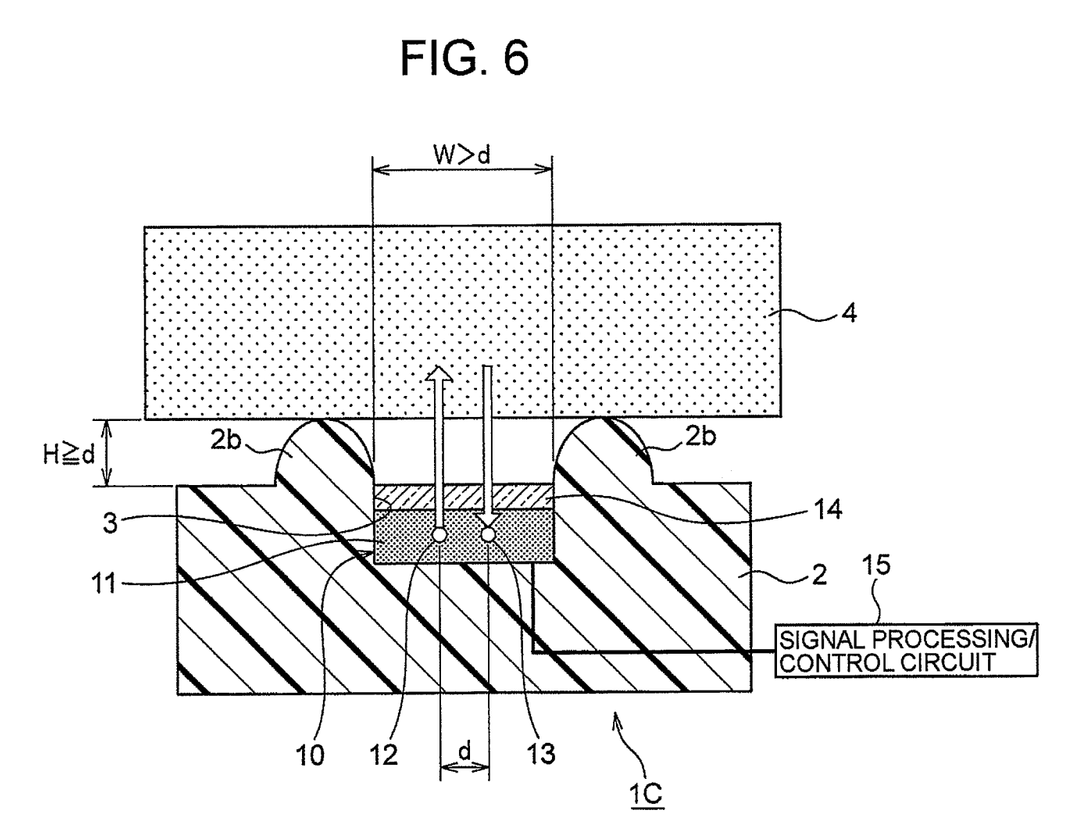
FIG. 6 is a schematic sectional view illustrating the biological information measuring apparatus according to the fourth embodiment of the present invention.

FIG. 6 is a schematic sectional view illustrating the biological information measuring apparatus according to the fourth embodiment of the present invention.

As shown in FIG. 6, the biological information measuring apparatus 1C comprises a receiving member 2 serving as the mounting unit. The receiving member 2 has a recess 3 formed therein. A beam-emitting type sensor device 10, which is capable of optically measuring biological information of the subject 4, is received in the recess 3.

In this embodiment of the present invention, the recess 3 has a smaller depth than that of the first to third embodiments of the present invention so that the upper surface of the anterior plate 14 of the beam-emitting type sensor device 10, which is received in the recess 3, is flush with the upper surface of the receiving member 2.

In this embodiment of the present invention, the projection 2b is integrally formed at the peripheral edge of the recess 3 with the receiving member 2. The projection 2b has a substantially semi-circular cross-section and a ring-shape in the plan view. The height "H" of the projection 2b is determined so as to be equal to or larger than a distance "d" between the respective centers of the laser diode 12 and the photodiode 13, and the opening width "W" of the projection 2b is determined so as to encompass at least the laser diode 12 and the photodiode 13.

Accordingly, the biological information measuring apparatus 1C according to the embodiment of the present invention is attached to the subject 4 in a state that, for example, the tip of a finger of the subject 4 is placed on the projection 2b so as to cross over the opening of the receiving member 2 in which the beam-emitting type sensor device 10 is received.

Then, the laser diode 12 is operated to emit the laser beam from the laser diode 12 and the laser beam passes through the anterior plate 14 to reach the tip of the finger of the subject 4, thereby measuring, for example, a blood velocity of the body tissue.

According to this embodiment of the present invention, the projection 2b is integrally formed at the peripheral edge of the recess 3 with the receiving member 2. In addition to the same technical effects as those of the first to third embodiments of the present invention, the projection 2b therefore restrict a mounting position of the beam-emitting type sensor device 10, thus making it possible to conduct easily amounting step for the beam-emitting type sensor device 10.

In this embodiment of the present invention, the projection 2b is described as having the substantially semi-circular cross-section. The present invention is not limited only to such an embodiment, but the projection may have a rectangular cross-section. In this embodiment of the present invention, the projection 2b is described as having the ring-shape in the plan view. However, there may be provided a plurality of projections, which are spaced apart from each other so as to be aligned along a predetermined shape.

In this embodiment of the present invention, the projection 2b is described as being integrally formed at the peripheral edge of the recess 3 with the receiving member 2. The present invention is not limited only to such an embodiment, but the projection, which has been previously formed of, for example, synthetic resin, may be connected to the receiving member 2 at the peripheral edge of the recess 3. This makes it possible to provide easily the projection.

When, in the embodiment of the present invention, a space in the projection 2b provided above the recess 3 in which the beam-emitting type sensor device 10 is received, is filled with material having a lower hardness than the site to be detected, for example transparent soft material such as flexible rubber, it is possible to prevent the space in the projection from being clogged with foreign substances such as dust. In view of medical purpose, when the space in the projection 2b provided above the recess 3 is filed with transparent liquid, it is possible to provide a stable condition between the beam-emitting type sensor device 10 and the skin of the subject 4, thus permitting a remarkably stable measurement of the human body. This may also apply to the subsequent embodiments in which the projection as formed is utilized.

Fifth Embodiment

Figure 7:
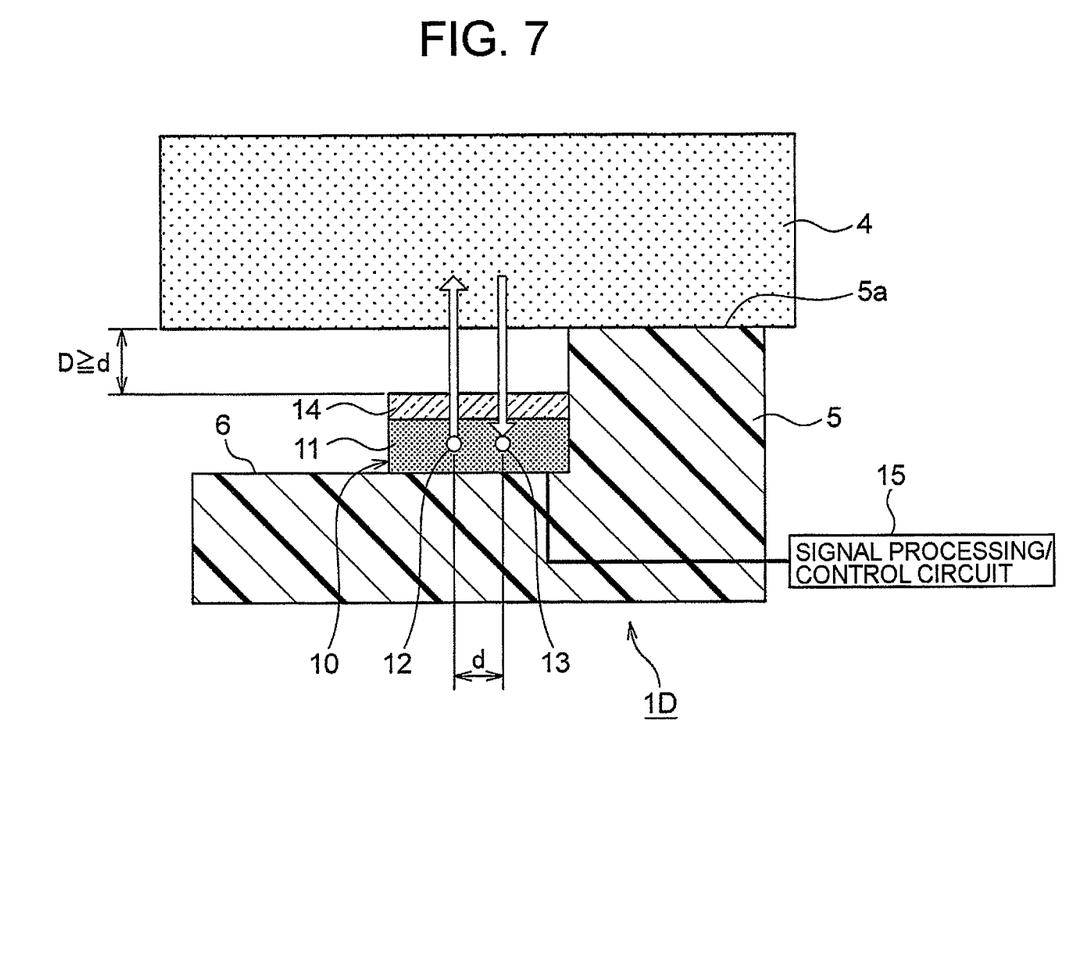
FIG. 7 is a schematic sectional view illustrating the biological information measuring apparatus according to the fifth embodiment of the present invention.

FIG. 7 is a schematic sectional view illustrating the biological information measuring apparatus according to the fifth embodiment of the present invention.

As shown in FIG. 7, the biological information measuring apparatus 1D comprises a mounting unit 5. The mounting unit 5 has a stepped portion 6 formed thereon. A beam-emitting type sensor device 10, which is capable of optically measuring biological information of the subject 4, is placed at the corner of the stepped portion 6.

A distance "D" between the contact surface 5a of the mounting unit 5, which is to come into contact with the subject 4, and the upper surface of the anterior plate 14 is determined so as to be equal to or larger than a distance "d" between the respective centers of the laser diode 12 and the photodiode 13.

In this embodiment of the present invention, a side of the beam-emitting type sensor device 10 is exposed, and a side plate is suitably placed on the above-mentioned side of the beam-emitting type sensor device 10 to protect this side.

According to the embodiment of the present invention, the mounting unit 5 has the stepped portion 6 formed thereon so that the stepped portion 6 provides at the side of the mounting unit 5 with an opening space, and the beam-emitting type sensor device 10 is placed on the stepped portion 6. In addition to the same technical effects as those of the first embodiment of the present invention, the beam-emitting type sensor device 10 can be mounted very easily.

Sixth Embodiment

Figure 8:
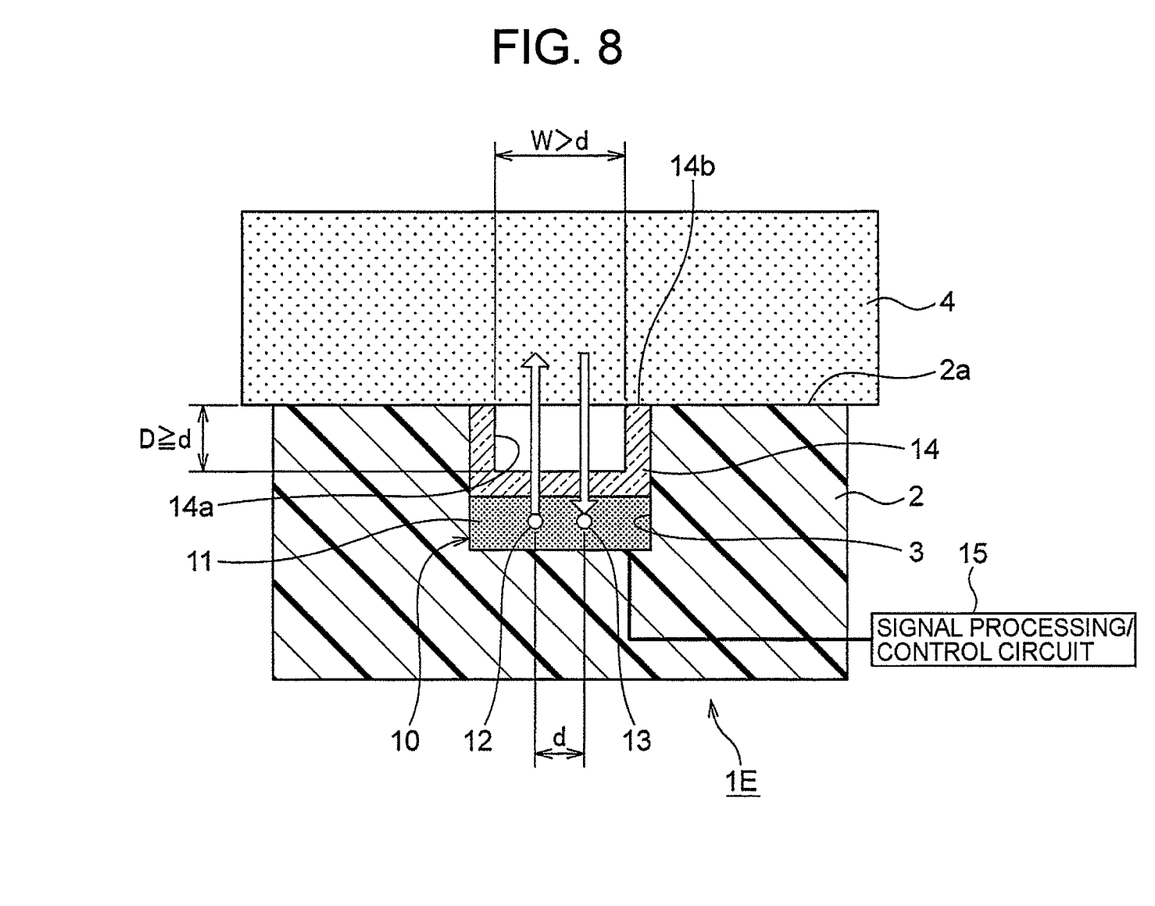
FIG. 8 is a schematic sectional view illustrating the biological information measuring apparatus according to the sixth embodiment of the present invention.

FIG. 8 is a schematic sectional view illustrating the biological information measuring apparatus according to the sixth embodiment of the present invention.

As shown in FIG. 8, the biological information measuring apparatus 1E comprises a receiving member 2 serving as the mounting unit. The receiving member 2 has a recess 3 formed therein, having a rectangular shape in the plan view. A beam-emitting type sensor device 10, which is capable of optically measuring biological information of the subject 4, is received in the recess 3.

In this embodiment of the present invention, the anterior plate 14 of the beam-emitting type sensor device 10 is provided with a recess 14a having a rectangular shape in the plan view. The anterior plate 14 is designed so that, when the beam-emitting type sensor device 10 is received in the recess 3, the opening end surface 14b of the anterior plate 14 is flush with the contact surface 2a of the receiving member 2.

When a distance between respective centers of the laser diode 12 and the photodiode 13 is determined as "d", a design is made so that the depth "D" of the recess 14a formed in the anterior plate 14 is to be equal to or larger than "d", and the recess 14a has the minimum opening width "W", which encompasses at least the laser diode 12 and the photodiode 13.

The biological information measuring apparatus 1E according to the embodiment of the present invention is attached to the subject 4 in a state that, for example, the tip of a finger of the subject 4 is placed on the contact surface 2a of the receiving member 2 so as to cross over the contact surface 2a of the receiving member 2 and the opening end surface 14b of the anterior plate 14. More specifically, a part of the anterior plate 14 is in contact with the subject 4, when measuring the biological information.

Then, the laser diode 12 is operated to emit the laser beam from the laser diode 12 and the laser beam passes through the anterior plate 14 to reach the tip of the finger of the subject 4, thereby measuring, for example, a blood velocity of the body tissue.

According to the embodiment of the present invention, a part of the anterior plate 14 is in contact with the subject 4, when measuring the biological information. Therefore, the pressure applied to a portion of the subject 4 to be measured cam be kept low in the same manner as the first embodiment of the present invention as described above, thus effectively preventing the constriction of the capillary vessels of the human body of the subject 4 to provide stable measurement results of the biological information and ensure a proper S/N ratio.

If, in this embodiment of the present invention, the recess 14a of the anterior plate 14 is provided at the opening peripheral edge thereof with a chamfered portion, in the same manner as the second embodiment of the present invention as described above, or the recess 14a thereof is provided at the opening peripheral edge thereof with a gently inclined surface, in the same manner as the third embodiment of the present invention as described above, it is possible to prevent the recess 14a from being clogged with foreign substances such as dust.

Seventh Embodiment

Figure 9:
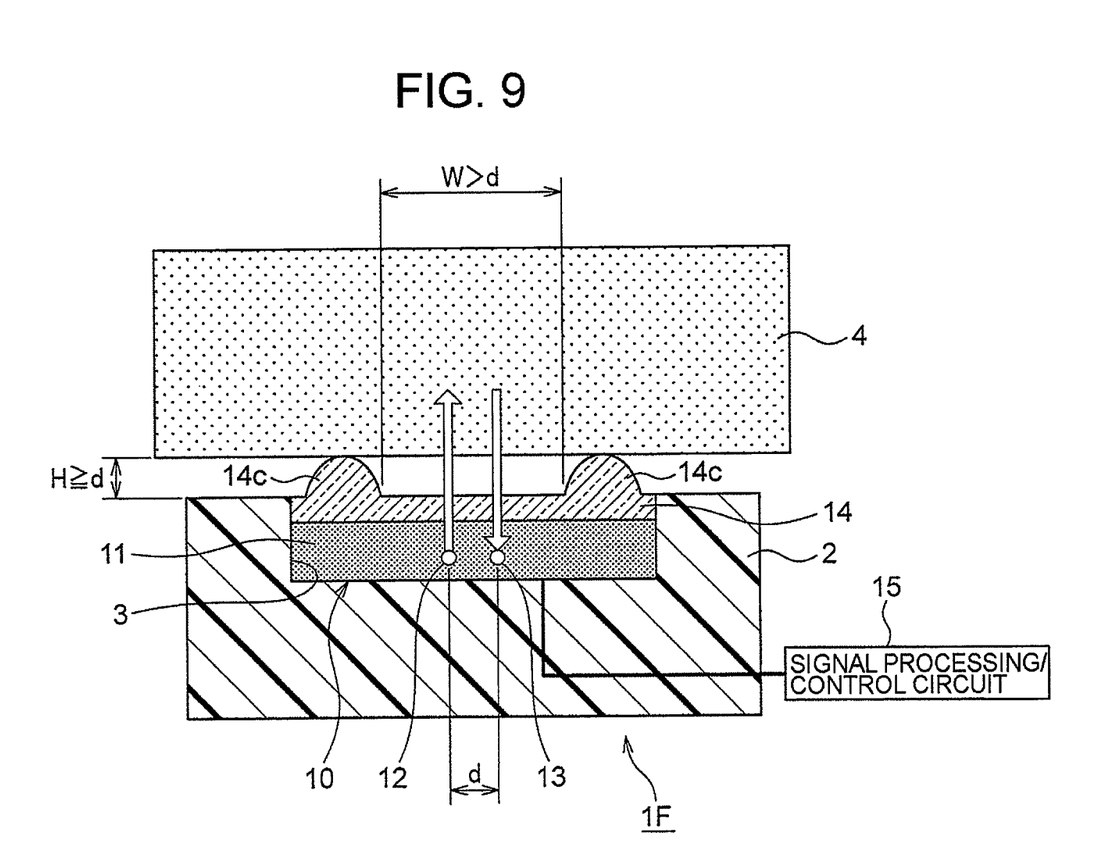
FIG. 9 is a schematic sectional view illustrating the biological information measuring apparatus according to the seventh embodiment of the present invention.

FIG. 9 is a schematic sectional view illustrating the biological information measuring apparatus according to the seventh embodiment of the present invention.

As shown in FIG. 9, the biological information measuring apparatus 1F comprises a receiving member 2 serving as the mounting unit. The receiving member 2 has a recess 3 formed therein. A beam-emitting type sensor device 10, which is capable of optically measuring biological information of the subject 4, is received in the recess 3.

In this embodiment of the present invention, the recess 3 has a smaller depth than that of the sixth embodiment of the present invention so that the upper surface of the anterior plate 14 of the beam-emitting type sensor device 10, which is received in the recess 3, is flush with the upper surface of the receiving member 2.

In this embodiment of the present invention, the projection 14c is integrally formed with the upper surface of the anterior plate 14. The projection 14c has a substantially semi-circular cross-section and a ring-shape in the plan view. The height "H" of the projection 14c is determined so as to be equal to or larger than a distance "d" between the respective centers of the laser diode 12 and the photodiode 13, and the opening width "W" of the projection 14c is determined so as to encompass at least the laser diode 12 and the photodiode 13.

Accordingly, the biological information measuring apparatus 1F according to the embodiment of the present invention is attached to the subject 4 in a state that, for example, the tip of a finger of the subject 4 is placed on the projection 14c so as to cross over the opening of the projection 14c of the anterior plate 14 of the beam-emitting type sensor device 10.

Then, the laser diode 12 is operated to emit the laser beam from the laser diode 12 and the laser beam passes through the anterior plate 14 to reach the tip of the finger of the subject 4, thereby measuring, for example, a blood velocity of the body tissue.

According to this embodiment of the present invention, the projection 14c is integrally formed with the upper surface of the anterior plate 14. In addition to the same technical effects as those of the sixth embodiment of the present invention, it is therefore possible to conduct easily a mounting step for the beam-emitting type sensor device 10.

In this embodiment of the present invention, the projection 14c is described as being integrally formed with the upper surface of the anterior plate 14. The present invention is not limited only to such an embodiment, but the projection, which has been previously formed of, for example, synthetic resin, may be connected to the upper surface of the anterior plate 14. This makes it possible to provide easily the projection. Further modifications of this embodiment are the same as those of the fourth embodiment of the present invention as described above, and the description of them will be omitted.

The present invention is not limited only to the above-described embodiments of the present invention, and may be modified. The respective embodiments of the present invention are described as measuring a blood velocity, but the present invention is not limited only to such embodiments, but may be used to measure, for example, a degree of blood oxygen saturation, utilizing difference in absorbance between oxygenated hemoglobin and reduced hemoglobin, and wavelength dependence of them. In this case, an LED may be used as a light source.

More specifically, a plurality of beams having the different wavelengths are emitted to the same site and an intensity of the reflected beams of the respective beams is measured. At this time, the beams are absorbed and reflected by hemoglobin included in blood of the subject 4, but the absorption rate varies between oxygenated hemoglobin and reduced hemoglobin. As a result, the intensity of the reflected beam varies based on a ratio of oxygenated (i.e., a degree of blood oxygen saturation). The respective absorbance of oxygenated hemoglobin and reduced hemoglobin reveals different characteristic properties in accordance with a wavelength of the beam as emitted. Therefore, the respective reflected beams of the plurality of beams having the different wavelengths, as emitted simultaneously differ from each other in intensity. More specifically, using, as a beam emitting device, a plurality of beams having the different wavelength permits to determine a degree of blood oxygen saturation.

It is also possible to measure the other information of chemical composition of biological fluid (i.e., blood or urine) than the above-mentioned degree of blood oxygen saturation by using, as the beam emitting device, a red LED or an infrared LED, which is capable of emitting a continuous spectrum beam of 700 to 1100 nm, and making an analysis by spectroscopy of absorbance based on the continuous spectrum beam. What is specifically to be analyzed may include, for example, erythrocyte, thrombocyte, total protein, total cholesterol, blood sugar level, and the like.

The present invention may be widely applicable as the blood velocity sensor to a field of medical engineering. Especially, the present invention enables the apparatus to be downsized to such an extent that it may always be attached to a user. Taking this advantage, the present invention may be applied to health management by for example mounting the apparatus to an earphone of a hearing aid or a wrist watch to monitor condition of health, or mounting the apparatus to a Western-style toilet seat to measure blood flow.

In the other field than the medical, the present invention is applicable to home electronics or mobile devices. The apparatus may be incorporated into for example a music headphone or a headset, or a controller for a game machine, to permit to predict a psychological state of a user, and make an automatic selection of music in accordance with the predicted psychological state or change contents of a game, thus providing various functions. Alternatively, the apparatus may be mounted on, for example, a steering wheel or a headrest of an automobile to monitor a condition of a driver or a passenger, thereby acquiring data to assist a safe driving such as a sleep-averting driving.

The present invention is not limited only to the embodiments as described above. The embodiments of the present invention are therefore to be considered as not restrictive, and any invention, which has substantially the same structure as the fundamental concept claimed in the appended claims and provides the similar functions, is considered as being within the scope of the present invention.

What is claimed is:

1. A biological information measuring apparatus, which comprises: a mounting unit having a contact surface, which is to come into contact with a surface of a subject, the mounting unit being provided with a recess formed thereon; a laser beam-emitting type sensor device being received in said recess of the mounting unit, said laser beam-emitting type sensor device being capable of optically measuring biological information of the subject, wherein:

a space is provided between the laser beam-emitting type sensor device and an extended plane of the contact surface of the mounting unit to ensure a non-contact area of the biological information measuring apparatus relative to the subject when measuring said biological information, and wherein:

the laser beam-emitting type sensor device comprises:

a sensor body received in the recess of the mounting unit; and a cover plate placed on the sensor body; and said space is provided between the cover plate of the laser beam-emitting type sensor device and the extended plane of the contact surface of the mounting unit.

2. The biological information measuring apparatus as claimed in claim 1, wherein:

said recess of the mounting unit is provided at an opening peripheral edge thereof with a chamfered portion.

3. The biological information measuring apparatus as claimed in claim 1 wherein:

the mounting unit having said recess is provided at the opening peripheral edge thereof with a curved surface.

4. The biological information measuring apparatus as claimed in claim 1, wherein:

the mounting unit having said recess is provided at the opening peripheral edge thereof with a projection having a contact portion, which serves as said contact surface, said contact portion having a semi-circular cross-section.

* * * * *